United States Patent [19]

Johnson et al.

[11] 4,156,296
[45] May 29, 1979

[54] GREAT (LARGE) TOE PROSTHESIS AND METHOD OF IMPLANTING

[75] Inventors: Kenneth A. Johnson, Rochester, Minn.; Allan Vegell, Warsaw, Ind.

[73] Assignee: Bio-Dynamics, Inc., Indianapolis, Ind.

[21] Appl. No.: 785,942

[22] Filed: Apr. 8, 1977

[51] Int. Cl.² .............................................. A61F 1/24
[52] U.S. Cl. ..................................... 3/1.91; 128/92 C
[58] Field of Search .................................. 3/1.9–1.913; 128/92 C

[56] References Cited

U.S. PATENT DOCUMENTS

| | | | |
|---|---|---|---|
| 3,506,982 | 4/1970 | Steffee | 3/1.91 |
| 3,965,489 | 6/1976 | Freeman et al. | 3/1.91 |
| 3,975,778 | 8/1976 | Newton | 3/1.91 |
| 3,992,726 | 11/1976 | Freeman et al. | 3/1.91 |
| 4,024,588 | 5/1977 | Janssen et al. | 3/1.91 |

OTHER PUBLICATIONS

"Silicone Rubber Implants for Replacement of Arthritic or Destroyed Joints in the Hand", by A. B. Swanson, Surgical Clinics of North America, vol. 48, No. 5, Oct. 1968, pp. 1119–1122.

Primary Examiner—Ronald L. Frinks
Attorney, Agent, or Firm—Woodard, Weikart, Emhardt & Naughton

[57] ABSTRACT

An endoprosthetic device for a prosthesis between metatarsal and phalangeal bones comprising proximal and distal components which are engageable with each other. The proximal component has a convex, part-spherical bearing surface and a stem projecting from this surface for securing the proximal component into the end of the first metatarsal. The distal component has a concave, part-spherical bearing surface and a stem projecting from this surface for securing the distal component into the end of the phalanx adjacent to the first metatarsal. The engagement of the two components forms a less-than-hemispherical articulation.

6 Claims, 6 Drawing Figures

GREAT (LARGE) TOE PROSTHESIS AND METHOD OF IMPLANTING

BACKGROUND OF THE INVENTION

1. Field of the Invention

This invention relates in general to prosthetic devices for the replacement of joints in human beings.

2. Description of the Prior Art

Prosthetic devices for use as joints to replace defective natural joints have been used by the medical profession for several years. Typically, such devices consist of two prosthetic members which are implanted into or attached to the anatomy of the subject at the location of the defective joint. The two members are constructed and positioned such that as the muscles and tendons exert a force on the contiguous natural bones, the movement of the prosthetic members with respect to each other simulates that of the natural joint. Unfortunately, many prostheses have been found to be impractical because the assembly of the components to one another after each component is implanted is difficult and often requires special surgical tools.

The device of Schultz, U.S. Pat. No. 3,760,427, discloses a prosthetic joint suitable for replacement of the metacarpophalangeal and the interphalangeal joints of the hand and for the knee. The device employs a socket element and a ball element which engage one another and the device is constructed to simulate the motion of a bony condyle. Each element has an intramedullary stem which is inserted into the medullary canal of a bone. One disadvantage of this device is the surgical difficulty of positioning the two elements relative to each other so that they function properly.

The device of Steffee, U.S. Pat. No. 3,506,982, also discloses a two-member, ball and socket articulation which incorporates a stem attached to each member for securing each member in place. Each stem is surgically inserted into intramedullary bone canals on each side of the joint being replaced such that the ball member is engaged by the socket member.

The device of Devas, U.S. Pat. No. 3,651,521, discloses a prosthetic device which comprises mutually-engageable male and female components and affords pivotal rotation in a plane.

Each of these prior art devices involve a style of ball and socket prosthetic joint with greater than 180° of engagement. Each device also incorporates mechanical limitations which reduce the degree of freedom of the joint to that of a hinge-like movement. A disadvantage of such hinge-type joints is that the flexion and extension motion of the appendage may expose sharp edges of the prosthetic device to the enclosing soft tissue and thus such devices are painful to the subject with even moderate use.

SUMMARY OF THE INVENTION

One embodiment of the present invention is an endoprosthetic device for the replacement of a joint in fingers and toes comprising mutually-engageable, proximal and distal components. The proximal component has a convex, part-spherical bearing surface and a stem projecting from the rear of the proximal component for affixing into a bone. The distal component has a concave, part-spherical bearing surface and a stem projecting from the rear of the distal component for affixing into a bone. The engagement of the convex, part-spherical bearing surface with the concave, part-spherical bearing surface forms a less-than-hemispherical area of contact wherein the engaging bearing surfaces are free to separate.

Another embodiment of the present invention might include a method of implanting a prosthetic device having mutually-engageable proximal and distal components for replacement of a metatarso-phalangeal joint which comprises the following steps. First, making an incision over the joint, removing a portion of bone from the end of the metatarsal adjacent the joint and inserting the proximal component into the metatarsal. Next, removing a portion of bone from the end of the proximal plalanx adjacent the joint and inserting the distal component into the proximal phalanx. Finally, closing the incision.

One object of the present invention is to provide an improved prosthetic joint design. Another object of the present invention is to provide an improved method of implanting a prosthesis.

Related objects and advantages of the present invention will be apparent from the following description.

DESCRIPTION OF THE PREFERRED EMBODIMENT

Figure 1:
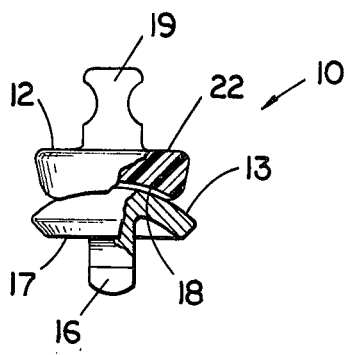
FIG. 1 is a fragmentary top view of a prosthetic device according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
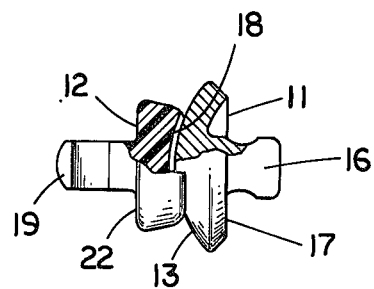
FIG. 2 is a fragmentary side view of the FIG. 1 prosthetic device.

Referring to FIGS. 1 and 2, there is illustrated an endoprosthetic device 10 comprising metatarsal component 11 and phalanx component 12. FIG. 1 is a top view of device 10 and FIG. 2 is a side view of device 10. The metatarsal component 11 has a convex, part-spherical bearing surface 13 and a stem 16 of generally-rectangular cross section projecting from the rear surface 17 of the component. The rear surface 17 of bearing surface 13 is a concave, part-spherical surface. Stem 16 is positioned approximately in the center of rear surface 17 and is perpendicular to rear surface 17. In the preferred embodiment, stem 16 is an integral part of metatarsal component 11. Although stem 16 could be attached to rear surface 17 by means of a screw or bolt, or possibly welded, greater component strength is provided by means of the single-piece construction of component 11.

The phalanx component 12 has a concave, part-spherical bearing surface 18 and a stem 19 of generally-rectangular cross section projecting from the rear surface 22 of the component. The rear surface 22 of bearing surface 18 is a generally-flat surface, externally circular in shape. Stem 19 is positioned in approximately the center of rear surface 22 and is perpendicular to rear surface 22. In the preferred embodiment, stem 19 is an intregal part of phalanx component 12 and affords the same advantages of improved strength as described for the metatarsal component 11.

The radius of convex bearing surface 13 of metatarsal component 11 is the same dimension as the radius of concave bearing surface 18 of phalanx component 12. Consequently, the metatarsal component 11 and phalanx component 12 are capable of engagement with one another at their bearing surfaces 13 and 18, respectively. Sliding motion is permitted between surfaces 13 and 18 in virtually all directions similar to a ball and socket connection.

Figure 3:
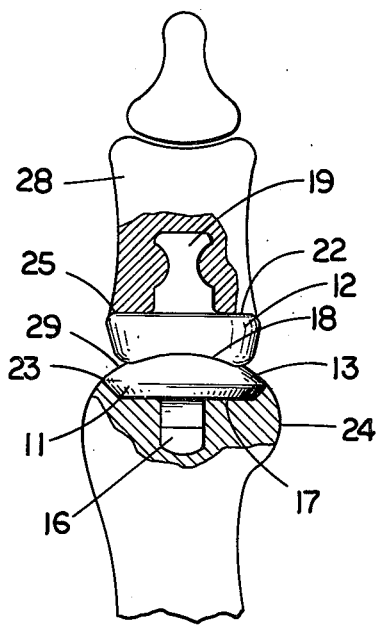
FIG. 3 is a fragmentary top view of the FIG. 1 prosthetic device as implanted into adjacent bones.
Figure 4:
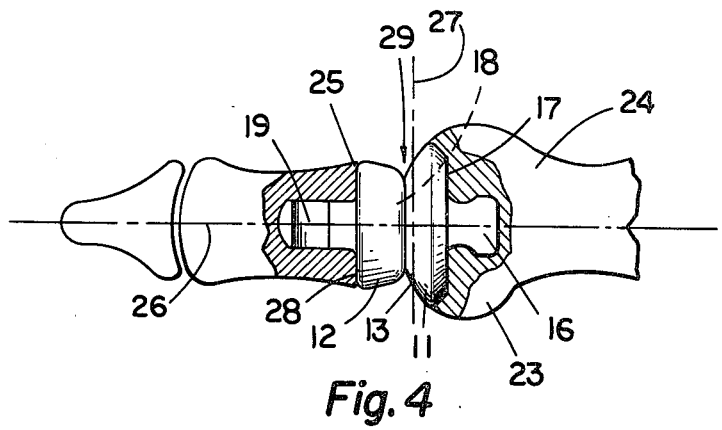
FIG. 4 is a fragmentary view of the device and bones of FIG. 3.

FIGS. 3 and 4 show the metatarsal component 11 and phalanx component 12 of endoprosthetic device 10 as implanted into their corresponding bones on each side of the first metatarso-phalangeal joint for which endoprosthetic device 10 is a replacement. One feature of device 10 is that the part-spherical bearing surface 13 of the metatarsal component 11 has a surface area which is noticeably larger than the surface area of the part-spherical bearing surface 18 of the phalanx component 12. This feature permits easy and comfortable articulation of the joint in that with normal flexing, the outer edge of surface 18 of phalanx component 12 will remain adjacent surface 13 and will not extend beyond the outermost edge of surface 13 into the surrounding tissue whereby such tissue might be pinched or irritated and thereby cause discomfort. Bearing surface 13 also provides a compatible surface against which the phalanx component 12 may slide and the size of surface 13 precludes component 12 from contacting the natural bone of the first metatarsal 24.

FIG. 3 is a skeletal representation of a top view and FIG. 4 is a skeletal representation of a side view of a human being's great (large) toe into which the device 10 has been implanted. The generally-rectangular cross section stem 16 of metatarsal component 11 is implanted into distal end 23 of the human being's first metatarsal 24. The generally-rectangular cross section stem 19 of phalanx component 12 is implanted into the proximal end 25 of the proximal phalanx 28 which is adjacent to the first metatarsal 24. The length of stems 16 and 19 projecting from surfaces 17 and 22, respectively, must be sufficient to allow each prosthetic component to be rigidly anchored into the corresponding bone and such stems may extend into the medullary canal of each bone. Thus, in one example of the invention the length of stem 16 is 0.28 inches and the length of stem 19 is 0.27 inches. Once the metatarsal component 11 and phalanx component 12 are implanted in the first metatarsal 24 and phalanx 28, respectively, their part-spherical bearing surfaces 13 and 18, respectively, are exposed and adjacent to each other and engage one another.

Bearing surfaces 13 and 18 are designed to be less than a hemisphere and will consequently form a less-than-hemispherical articulation wherein there is no locking of one member to the other. There are no intricate features which interlock the metatarsal component 11 with the phalanx component 12 and bearing surfaces 13 and 18 of the two components are held together due to the nature of the anatomy of the toe and the surrounding tissue. Similarly, proper joint alignment is provided by the soft tissue of the toe which surrounds the prosthetic joint. Surface of engagement 29 which is a common interface for both bearing surfaces 13 and 18 is the surface where sliding motion occurs between the two components 11 and 12, as the toe is moderately flexed, and with most natural toe motions the toe will be only moderately flexed. However, it is possible for the toe to be flexed to such a degree that on one side of surface of engagement 29 the two components will separate slightly. On the other side of the surface of engagement the two components will remain in contact. The metatarsal and phalanx bones are prepared in such a way prior to anchoring the prosthetic components in place that the contours of the exposed surfaces (of both the bones and prosthesis) are generally smooth and free of sharp edges. Consequently, flexing the prosthetic joint will not be a painful movement.

As is illustrated in FIGS. 3 and 4, the engaging bearing surfaces 13 and 18 are free to slide relative to each other in a universal, unrestrained manner in that there are not stop surfaces present on or adjacent the bearing surfaces of either component. Any limitation to the freedom of movement would thus be the result of the tissue and ligaments surrounding the prosthetic joint. A further feature of this prosthesis is the dimensional relationship between convex bearing surface 13 and metatarsal component 11. Longitudinal axis line 26 extends through the approximate center of each component and is substantially coincident with the longitudinal axes of the bones (metatarsal 24 and phalanx 28). Perpendicular to longitudinal axis line 26 is transverse axis line 27 and consequently, any plane which is both parallel to line 27 and perpendicular to line 26 defines a suitable plane for measuring a transverse dimension. As illustrated, the maximum transverse dimension of bearing surface 13 is equal to the maximum transverse dimension of the metatarsal component 11.

Figure 5:
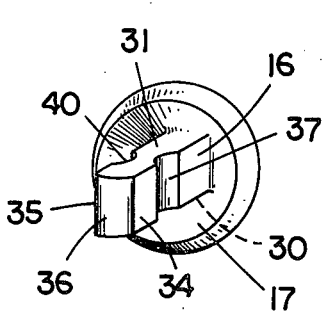
FIG. 5 is a perspective view of the metatarsal component of the FIG. 1 prosthetic device.

FIG. 5 is a perspective view of metatarsal component 11 showing the generally-rectangular cross section stem 16 in greater detail. Stem 16 has two planar surfaces 30 and 31 longitudinally extending from rear surface 17 to end 36 and sides 34 and 35 extending between surfaces 30 and 31. Sides 34 and 35 each have a concave recess 37 and 40, respectively, which are positioned approximately half way between rear surface 17 and end 36. Concave recesses 37 and 40 extend from surfaces 30 to surface 31 and serve to anchor metatarsal component 11 in place when implanted into the first metatarsal 24, as shown in FIG. 4.

Figure 6:
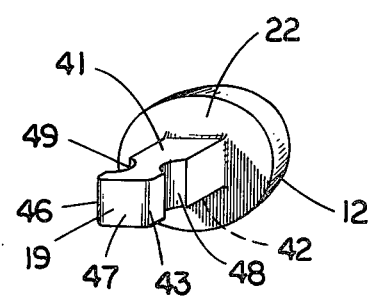
FIG. 6 is a perspective view of the phalanx component of the FIG. 1 prosthetic device.

FIG. 6 is a perspective view of phalanx component 12 showing the generally-rectangular cross section stem 19 in greater detail. Stem 19 has two planar surfaces 41 and 42, longitudinally extending from rear surface 22 to end 47, and sides 43 and 46 extending between surfaces 41 and 42. Sides 43 and 46 each have a concave recess 48 and 49, respectively, which are positioned approximately half way between rear surface 22 and end 47. Concave recesses 48 and 49 extend between surfaces 41 and 42 and serve to anchor phalanx component 12 in place when implanted into phalanx 28, as shown in FIG. 3.

The implant procedure for endoprosthetic device 10 is done in an operating room with suitable operating room sterility precautions. First, the foot is sterilely prepared and the area surrounding the metatarso-phalangeal joint is expressed of blood and is kept blood-free by means of a tourniquet. Next a dorsomedial incision is made over the metatarso-phalangeal joint and the joint capsule is opened. Depending upon the pathologic reason for the prosthetic insertion, the soft tissue about the joint is manipulated in such a way as to achieve the best result. Before prosthetic device 10 can be inserted, a portion of bone must first be removed from the distal end 23 of first metatarsal 24 (see FIGS. 3 and 4). As metatarsal component 11 is inserted, rear surface 17 will come to rest on the distal end 23 and then metatarsal component 11 is fixed to the first metatarsal 24 by the use of a suitable polymerizing grouting material such as methyl methacrylate. This material fills the various voids which might be present between the bone and the component stem and then the material hardens to rigidly bond the component in place. The next step is to remove the base of the proximal phalanx 28 at end 25 with a power-driven saw. Then after burr molding of the area, phalanx component 12 is inserted until rear surface 22 comes to rest on end 25. Phalanx component 12 is then fixed to phalanx 28 by the use of a suitable polymerizing grouting material such as methyl methacrylate. Finally, the soft tissue of the toe is closed around both components 11, 12 of prosthetic device 10 in such a way as to give proper realignment of the prosthesis.

The preferred material for metatarsal component 11 is a substantially, physiologically inert metal such as orthochrome and the preferred material for phalanx component 12, polyethylene.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An endoprosthetic device for replacement of a joint in fingers and toes which comprises only two components, said two components being mutually engageable and including a proximal component and a distal component, the proximal component having a convex, part-spherical bearing surface and a first stem projecting from the rear of said proximal component for affixing into a bone, the maximum transverse dimension of said convex bearing surface equaling the maximum transverse dimension of said proximal component, the distal component having a concave, part-spherical bearing surface and a second stem projecting from the rear of said distal component for affixing into a bone, said convex, part-spherical bearing surface having a surface area noticeably larger than the surface area of said concave, part-spherical bearing surface, the engagement of the convex, part-spherical bearing surface with the concave, part-spherical bearing surface forming a less-than-hemispherical area of contact, said engaging bearing surfaces being free to slide relative to each other in a universal manner and being free of any stop surfaces.

2. The endoprosthetic device of claim 1 in which each stem has a pair of concave recesses in spaced-apart relationship.

3. The endoprosthetic device of claim 2 in which the proximal components is made of a substantially, physiologically inert metal and the distal component is made of polyethylene.

4. The endoprosthetic device of claim 3 in which the proximal and distal components are of a size suitable for a prosthesis of the metatarso-phalangeal joint of the first metatarsal.

5. A method of implanting a prosthetic device having only two components, a proximal component and a distal component, into a metatarsal and a proximal phalanx for replacement of a metatarso-phalangeal joint which comprises the steps of:
    making a dorsomedial incision over the metatarso-phalangeal joint;
    removing a portion of bone from the end of the metatarsal adjacent said joint;
    inserting the proximal component into the metatarsal at said end, said proximal component having a convex, part-spherical bearing surface, the maximum transverse dimension of said convex, part-spherical bearing surface equaling the maximum transverse dimension of said proximal component;
    removing a portion of bone from the end of the proximal phalanx adjacent said joint;
    inserting the distal component into the proximal phalanx at said end, said distal component having a concave, part-spherical bearing surface with a surface area noticeably smaller than the surface area of the convex, part-spherical bearing surface of the proximal component, the engagement of said bearing surfaces forming a less-than-hemispherical area of contact, said engaging bearing surfaces being free to slide relative to each other in a universal manner and being free of any stop surfaces; and
    closing the incision.

6. The method of implanting a prosthetic device as recited in claim 5 comprising the additional steps of affixing each component into the bone by means of a grouting compound subsequent to each inserting step.

* * * * *